(12) United States Patent
Park et al.

(10) Patent No.: US 11,357,861 B2
(45) Date of Patent: Jun. 14, 2022

(54) PROTEIN COMPLEX COMPRISING NON-PEPTIDYL POLYMER-COUPLED FATTY ACID DERIVATIVE COMPOUND AS LINKER AND PREPARATION METHOD THEREFOR

(71) Applicant: HANMI PHARM. CO., LTD., Hwaseong-si (KR)

(72) Inventors: Su Yeon Park, Hwaseong-si (KR); Ji Young Song, Hwaseong-si (KR); Eun Jung Kim, Hwaseong-si (KR); Jong Min Lee, Hwaseong-si (KR); Jong-Soo Lee, Hwaseong-si (KR); Dae Jin Kim, Hwaseong-si (KR)

(73) Assignee: HANMI PHARM. CO., LTD, Hwaseong (KR)

( * ) Notice: Subject to any disclaimer, the term of this patent is extended or adjusted under 35 U.S.C. 154(b) by 0 days.

(21) Appl. No.: 16/647,115

(22) PCT Filed: Oct. 1, 2018

(86) PCT No.: PCT/KR2018/011626
§ 371 (c)(1),
(2) Date: Mar. 13, 2020

(87) PCT Pub. No.: WO2019/066609
PCT Pub. Date: Apr. 4, 2019

(65) Prior Publication Data
US 2020/0276317 A1 Sep. 3, 2020

(30) Foreign Application Priority Data
Sep. 29, 2017 (KR) .................... 10-2017-0127790

(51) Int. Cl.
*A61K 47/56* (2017.01)
*A61K 47/54* (2017.01)
*C07K 14/62* (2006.01)
*C08G 65/325* (2006.01)

(52) U.S. Cl.
CPC ............. *A61K 47/56* (2017.08); *A61K 47/54* (2017.08); *C07K 14/62* (2013.01); *C08G 65/325* (2013.01)

(58) Field of Classification Search
None
See application file for complete search history.

(56) References Cited

U.S. PATENT DOCUMENTS

| 8,691,755 B2 | 4/2014 | Barrack et al. |
| 2011/0201754 A1 | 8/2011 | Kitagawa et al. |

FOREIGN PATENT DOCUMENTS

| EP | 3 384 935 A1 | 10/2018 |
| KR | 10-2003-0036081 A | 5/2003 |
| KR | 10-2005-0025974 A | 3/2005 |
| KR | 10-2017-0104409 A | 9/2017 |
| WO | 2017/095201 A1 | 6/2017 |

OTHER PUBLICATIONS

Eizo Sada et al., "Resistance to Proteolysis of Antibody Ligands Modified with Polyethylene Glycol", Journal of Fermentation and Bioengineering, 1991, pp. 137-139, vol. 71, No. 2.
Stephen Curry et al., "Fatty acid binding to human serum albumin: new insights from crystallographic studies", Biochimica et Biophysica Acta, 1999, pp. 131-140, vol. 1441.
International Search Report for PCT/KR2018/011626, dated Jan. 3, 2019.
Kim et al., "Protein complex using fatty acid derivative, and preparation method", Hanmi Pharm Co., Ltd., Jun. 8, 2017 (25 pages total) (CAPLUS printout only).

*Primary Examiner* — Po-Chih Chen
(74) *Attorney, Agent, or Firm* — Sughrue Mion, PLLC (57) ABSTRACT

Provided are a protein conjugate in which a physiologically active polypeptide is linked to a biocompatible material via a non-peptidyl polymer-coupled fatty acid derivative compound serving as a linker, exhibiting an increased duration of physiological activity compared to natural forms and a preparation method therefor. Since an increase in serum half-life of the physiologically active polypeptide of the protein conjugate, in which the biocompatible material, the non-peptidyl polymer-coupled fatty acid derivative compound, and the physiologically active polypeptide are linked, is proved, the protein conjugate may be widely used in the field of protein drugs.

8 Claims, 2 Drawing Sheets

[FIG. 1]

M: size marker
1: POLYPEPTIDE, INSULIN
2: INSULIN-COUPLED FATTY ACID DERIVATIVE
3: IMMUNIGLOBULIN FC
4: IIMMUNNOGLOBULIN FC-FATTY ACID DERIVATIVE-INSULIN CONJUGATE

PROTEIN COMPLEX COMPRISING NON-PEPTIDYL POLYMER-COUPLED FATTY ACID DERIVATIVE COMPOUND AS LINKER AND PREPARATION METHOD THEREFOR

CROSS REFERENCE TO RELATED APPLICATIONS

This application is a National Stage of International Application No. PCT/KR2018/011626 filed Oct. 1, 2018, claiming priority based on Korean Patent Application No. 10-2017-0127790 filed Sep. 29, 2017.

TECHNICAL FIELD

The present invention relates to a protein complex, in which a physiologically active polypeptide is linked to a biocompatible material via a non-peptidyl polymer-coupled fatty acid derivative compound, exhibiting an increased duration of physiological activity compared to natural forms, and a preparation method thereof.

BACKGROUND ART

In general, physiologically active polypeptides are easily denatured due to low stability, degraded by proteases in the blood, and easily removed by the kidneys or liver. Accordingly, in order to maintain the blood concentration and titer of a protein drug containing a physiologically active polypeptide as a pharmacological component, the protein drug needs to be administered frequently to a patient. However, since most of the protein drugs are administered to patients in the form of injection, frequent administration via injection to maintain blood concentration of the physiologically active polypeptide causes severe pain to the patients. In order to resolve these problems, efforts have been made to maximize the efficacy of protein drugs by increasing blood stability of the protein drugs and by maintaining the blood concentration thereof at a high level for a long period of time. However, these long-acting formulations of protein drugs should not induce immune responses in patients while increasing the stability of the protein drugs.

As a method of stabilizing proteins, inhibiting contact with proteases, and reducing renal clearance, a protein pegylation method where a highly soluble polymer such as polyethylene glycol (hereinafter, referred to as "PEG") is chemically added to the surfaces of protein drugs has been conventionally used. Since PEG non-specifically binds to a specific site or various sites of a target protein and increases solubility thereof, it has been known to be effective in stabilizing proteins and preventing hydrolysis of proteins without causing any particular side effects (Sada et al., J. Fermentation Bioengineering, 71: pp 137-139, 1991).

Free fatty acid is known to have a binding affinity to human serum albumin (HAS) (Curry S. et al., Biochim, Biophys. Acta, 1441: 131-140, 1999). Due to this characteristic, when administered into the human body in a combined form with a therapeutic drug (e.g., protein, peptide, and siRNA), the fatty acid binds to serum albumin having a binding affinity to the fatty acid by noncovalent bonds. Albumin-drug complexes formed as described above are known to increase serum half-life by decreasing hydrolysis of proteins or absorption rates of cell membranes. Levemir® (insulin detemir, Novo Nordisk) and Victoza® (liraglutide [rDNA origin] injection, Novo Nordisk) have been known as therapeutic agents that bind to a fatty acid derivative and are approved by the Food and Drug Administration (FDA) and the European Medical Agency (EMA).

DESCRIPTION OF EMBODIMENTS

Technical Problem

An object of the present invention is to provide a non-peptidyl polymer-coupled fatty acid derivative compound, a stereoisomer thereof, or a pharmaceutically acceptable salt thereof.

Another object of the present invention is to provide a protein complex in which a physiologically active polypeptide and a biocompatible material are linked, by covalent bonds, to a non-peptidyl polymer-coupled fatty acid derivative compound serving as a linker.

Another object of the present invention is to provide a method of preparing the protein complex.

Solution to Problem

An aspect of the present invention is to provide a non-peptidyl polymer-coupled fatty acid derivative compound represented by Formula 1 below, a stereoisomer thereof, or a pharmaceutically acceptable salt thereof.

Formula 1

In Formula 1 above, $L_1$ to $L_3$ are each independently a linear or branched $C_{1-6}$ alkylene, $R_1$ and $R_2$ may each independently be selected from the group consisting of 2,5-dioxopyrrolidinyl, 2,5-dioxopyrrolyl, aldehyde, maleimide, a $C_{6-20}$ aryl disulfide, a $C_{5-20}$ heteroaryl disulfide, vinyl sulfone, thiol, halogenated acetamide, succinimide, p-nitrophenyl carbonate, a $C_{7-10}$ alkynyl, orthopyridyl disulfide (OPSS), halogen, and a derivative thereof, m1 to m3 are each independently a natural number of 1 to 2400, and n is a natural number of 1 to 40.

According to an embodiment, $R_1$ and $R_2$, which correspond to reactive groups of the non-peptidyl polymer-coupled fatty acid derivative compound included in a protein complex according to the present invention, may each independently be maleimide, N-hydroxysuccinimide, succinimide, a $C_{1-4}$ alkylene aldehyde, orthopyridyl disulfide (OPSS), iodoacetamide (IA), halogenated acetamide including bromide, fluorine, chlorine, or astatine instead of iodine, difluorocyclooctyne (DIFO), dibenzocyclooctyne (DIBO), dibenzo-aza-cyclooctyne (DIBAC or DBCO), biarylazacyclooctynones (BARAC), tetramethylthiacycloheptyne (TMTH), bicyclononyne (BCN), Sondheimer diyne, cyclooctyne (OCT), monofluorinated cyclooctyne (MOFO), dimethoxyazacyclooctyne (DIMAC), 2,3,6,7-tetramethoxy-DIBO (TMDIBO), sulfonylated DIBO (S-DIBO), carboxymethylmonobenzocyclooctyne (COMBO), pyrrolocyclooctyne (PYRROC), or alkyne.

Another aspect of the present invention is to provide a protein complex in which a physiologically active polypeptide and a biocompatible material are linked, by covalent bonds, to a non-peptidyl polymer-coupled fatty acid derivative compound represented by Formula 2 below and serving as a linker.

Formula 2

In Formula 2 above, $L_1$ to $L_3$ are each independently a linear or branched $C_{1-6}$ alkylene, Non-Pep is a non-peptidyl polymer, m1 and m2 are each independently a natural number of 1 to 2400, and n is a natural number of 1 to 40.

According to an embodiment, in the protein complex according to the present invention, the non-peptidyl polymer-coupled fatty acid derivative compound may have two reactive groups each linked to a fatty acid backbone thereof directly or via a linker and may be linked to the physiologically active polypeptide and the biocompatible material via the reactive groups, respectively. Specifically, the non-peptidyl polymer-coupled fatty acid derivative compound may serve as a linker for linking the physiologically active polypeptide to the biocompatible material.

According to another embodiment, the non-peptidyl polymer-coupled fatty acid derivative compound included in the protein complex according to the present invention may have two or more reactive groups each linked to a fatty acid backbone thereof directly or via a linker and may be linked to the physiologically active polypeptide and the biocompatible material via the reactive linkers, respectively.

According to any one of the above-described embodiments, the non-peptidyl polymer-coupled fatty acid derivative compound included in the protein complex according to the present invention, as a linker, may include a $C_{1-3}$ alkylamino and a $(C_{1-3}$ alkoxy$)_n(C_{1-3}$ alkylamino) chain.

According to any one of the above-described embodiments, a non-peptidyl polymer of the non-peptidyl polymer-coupled fatty acid derivative compound included in the protein complex according to the present invention may be a polyethylene glycol homopolymer, a polypropylene glycol homopolymer, an ethylene glycol-propylene glycol copolymer, a polyoxyethylated polyol, a polyvinyl alcohol, a polysaccharide, a dextran, a polyvinyl ethyl ether, a biodegradable polymer, a lipid polymer, a fatty acid, chitin, hyaluronic acid, and any combination thereof.

According to any one of the above-described embodiments, the non-peptidyl polymer of the non-peptidyl polymer-coupled fatty acid derivative compound included in the protein complex according to the present invention may be polyethylene glycol including 1 to 2400 repeating units.

According to any one of the above-described embodiments, at least one conjugate of the physiologically active polypeptide and the non-peptidyl polymer-coupled fatty acid derivative compound is linked to a unit of the biocompatible material included in the protein complex according to the present invention.

According to any one of the above-described embodiments, the physiologically active polypeptide included in the protein complex according to the present invention may be a hormone, a cytokine, an interleukin, an interleukin-binding protein, an enzyme, an antibody, a growth factor, a transcription factor, a blood factor, a vaccine, a structural protein, a ligand protein, a receptor, a cell surface antigen, or a receptor antagonist.

According to any one of the above-described embodiments, the physiologically active polypeptide included in the protein complex according to the present invention may be selected from the group consisting of: incretins regulating body weights and blood glucose levels in the stomach and intestines such as glucagon-like peptide-1 (GLP-1), glucagon-like peptide-2 (GLP-2), glucagon, gastric inhibitory polypeptide (GIP), oxyntomodulin, xenin, insulin, cholecystokinin (CCK), amylin, gastrin, ghrelin, and peptide YY (PYY); adipokines secreted from adipose such as leptin, adiponectin, adipolin, apelin, and cartonectin; neuropeptides secreted from the brain such as kisspeptin and nesfatin-1; peptides or proteins secreted from muscles such as irisin, myonectin, decorin, follistatin, and musdin; vasoactive intestinal peptide, natriuretic peptide, granulocyte colony stimulating factor (G-CSF), human growth hormone (hGH), erythropoietin (EPO), growth hormone releasing hormone, growth hormone releasing peptide, interferons, interferon receptors, G-protein-coupled receptors, interleukins, interleukin receptors, enzymes, interleukin-binding protein, cytokine-binding protein, macrophage activating factor, macrophage peptide, B cell factor, T cell factor, protein A, allergy inhibitor, cell necrosis glycoprotein, immunotoxin, lymphotoxin, tumor necrosis factor, tumor suppressor, metastasis growth factor, α-1 antitrypsin, albumin, α-lactalbumin, apolipoprotein-E, highly glycosylated erythropoietin, angiopoietins, hemoglobin, thrombin, thrombin receptor activating peptide, thrombomodulin, blood factors VII, VIIa, VIII, IX and XIII, plasminogen activating factor, fibrin-binding peptide, urokinase, streptokinase, hirudin, protein C, C-reactive protein, lenin inhibitor, collagenase inhibitor, superoxide dismutase, platelet-derived growth factor, epithelial growth factor, epidermal growth factor, angiostatin, angiotensin, bone growth factor, bone stimulating protein, calcitonin, atriopeptin, cartilage inducing factor, elcatonin, connective tissue activating factor, tissue factor pathway inhibitor, follicle stimulating hormone, luteinizing hormone, luteinizing hormone releasing hormone, nerve growth factor, parathyroid hormone, relaxin, secretin, somatomedin, insulin-like growth factor, adrenocortical hormone, cholecystokinin, pancreatic polypeptide, gastrin releasing peptide, corticotropin releasing factor, thyroid stimulating hormone, autotaxin, lactoferrin, myostatin, cell surface antigens, virus derived vaccine antigens, monoclonal antibodies, polyclonal antibodies, and antibody fragments.

According to any one of the above-described embodiments, the physiologically active polypeptide according to the present invention may activate two or more receptors simultaneously.

According to any one of the above-described embodiments, the physiologically active polypeptide according to the present invention is not a naturally occurring polypeptide but selected from derivatives of naturally occurring physiologically active polypeptides. The derivatives of physiologically active polypeptides refer to polypeptides whose binding affinity to a receptor or physicochemical property is altered, i.e., water solubility is increased or immunogenicity is modified, via chemical modification such as substitution, insertion, and deletion of an amino acid, glycosylation, deglycosylation, unnatural amino acid insertion, ring insertion, and methyl residue insertion, and may also include synthetic peptides modified to have binding affinities to two or more different receptors.

According to any one of the above-described embodiments, the biocompatible material included in the protein complex according to the present invention may be selected from the group consisting of polyethylene glycol (PEG), cholesterol, albumin and a fragment thereof, an albumin-binding material, a polymer of a particular amino acid sequence as a repeating unit, an antibody, an antibody fragment, an FcRn-binding material, in vivo connective tissue or a derivative thereof, a nucleotide, fibronectin, transferrin, saccharide, a polymer, and any combination thereof.

According to any one of the above-described embodiments, the FcRn-binding material included in the protein complex according to the present invention may be a polypeptide including an immunoglobulin Fc region.

According to any one of the above-described embodiments, the immunoglobulin Fc region included in the protein complex according to the present invention may be aglycosylated.

According to any one of the above-described embodiments, the immunoglobulin Fc region included in the protein complex according to the present invention may include a hinge region.

According to any one of the above-described embodiments, the immunoglobulin Fc region included in the protein complex according to the present invention may be selected from the group consisting of IgG, IgA, IgD, IgE, IgM, any combination thereof, and any hybrid thereof.

According to any one of the above-described embodiments, the immunoglobulin Fc region included in the protein complex according to the present invention may be an IgG4 Fc fragment.

Still another aspect of the present invention is to provide a method of preparing a protein complex including: (a) linking a physiologically active peptide to a biocompatible material via a non-peptidyl polymer-coupled fatty acid derivative compound including two or more reactive groups and represented by Formula 3 below; and (b) separating a protein complex as a reaction product obtained in step (a):

Formula 3

In Formula 3 above, $L_1$, $L_2$, $L_3$, $R_1$, $R_2$, Non-Pep, m1 to m3, and n are as defined above.

According to an embodiment, step (a) of the preparation according to the present invention may include: (a1) linking one of the biocompatible material and the physiologically active polypeptide to one reactive group of the non-peptidyl polymer-coupled fatty acid derivative compound; (a2) separating a conjugate in which the biocompatible material or the physiologically active polypeptide is linked to the non-peptidyl polymer-coupled fatty acid derivative compound from a reaction mixture of step (a1); and (a3) linking the other of the biocompatible material and the physiologically active polypeptide to the other reactive group of the non-peptidyl polymer-coupled fatty acid derivative compound of the conjugate separated in step (a2) to prepare a protein complex in which the two or more reactive groups of the non-peptidyl polymer-coupled fatty acid derivative compound are linked respectively to the physiologically active polypeptide and the biocompatible material.

According to another embodiment, steps (a1) and (a3) of the preparation method according to the present invention may be performed in the presence of a reducing agent.

According to any one of the above-described embodiments, in the preparation method according to the present invention, the reducing agent may be sodium cyanoborohydride ($NaCNBH_3$), sodium borohydride, dimethylamine borate, picoline borane complex, or borane pyridine.

According to any one of the above-described embodiments, in the preparation method according to the present invention, a reaction molar ratio of the physiologically active polypeptide to the non-peptidyl polymer-coupled fatty acid derivative compound may be from 1:1 to 1:20 and a reaction molar ratio of the biocompatible material to the non-peptidyl polymer-coupled fatty acid derivative compound may be from 1:1 to 1:20 in step (a1).

According to any one of the above-described embodiments, in the preparation method according to the present invention, a reaction molar ratio of the conjugate separated in step (a2) to the biocompatible material or the physiologically active polypeptide may be from 1:0.5 to 1:20 in step (a3).

Advantageous Effects of Disclosure

Since the non-peptidyl polymer-coupled fatty acid derivative compound is proved to increase a serum half-life of a physiologically active polypeptide when administered in the form of a protein complex, in which a physiologically active polypeptide disposed at one end, the non-peptidyl polymer-coupled fatty acid derivative compound used as a linker, and a biocompatible material are sequentially linked by covalent bonds, the non-peptidyl polymer-coupled fatty acid derivative compound according to the present invention may be widely used in the field of protein drugs.

BEST MODE

An aspect of the present invention provides a non-peptidyl polymer-coupled fatty acid derivative compound represented by Formula 1 below, a stereoisomer thereof, or a pharmaceutically acceptable salt thereof.

aldehyde, acetaldehyde, propionaldehyde, butylaldehyde, orthopyridyl disulfide (OPSS), iodoacetamide, halogenated acetamide including bromide, fluorine, chlorine, or astatine instead of iodine, difluorocyclooctyne (DIFO), dibenzocyclooctyne (DIBO), dibenzo-aza-cyclooctyne (DIBAC or DBCO), biarylazacyclooctynones (BARAC), tetramethylthiacycloheptyne (TMTH), bicyclononyne (BCN), Sondheimer diyne, cyclooctyne (OCT), monofluorinated cyclooctyne (MOFO), dimethoxyazacyclooctyne (DIMAC), 2,3,6,7-tetramethoxy-DIBO (TMDIBO), sulfonylated DIBO (S-DIBO), carboxymethylmonobenzocyclooctyne (COMBO), pyrrolocyclooctyne (PYRROC), or alkyne, but is not limited thereto.

For example, the m1 to m3 may each independently be a natural number of 1 to 2400, specifically, m1 and m2 may each independently be a natural number of 1 to 20, a natural number of 1 to 10, or a natural number of 1 to 5, but are not limited thereto. The m3 may be a natural number of 20 to 500, a natural number of 10 to 500, a natural number of 10 to 100, or a natural number of 100 to 500, but is not limited thereto.

For example, the n may be a natural number of 1 to 40, specifically a natural number of 4 to 30, more specifically a natural number of 10 to 25, but is not limited thereto.

Another aspect of the present invention provides a protein complex in which a physiologically active polypeptide disposed at one end; a non-peptidyl polymer-coupled fatty acid derivative compound represented by Formula 2 below as a linker; and a biocompatible material are sequentially linked by covalent bonds.

Formula 1

Formula 2

In Formula 1 above, $L_1$ to $L_3$ are each independently a linear or branched $C_{1-6}$ alkylene, $R_1$ and $R_2$ are each independently selected from the group consisting of 2,5-dioxopyrrolidinyl, 2,5-dioxopyrrolyl, aldehyde, maleimide, a $C_{6-20}$ aryl disulfide, a $C_{5-20}$ heteroaryl disulfide, vinyl sulfone, thiol, halogenated acetamide, succinimide, p-nitrophenyl carbonate, a $C_{7-10}$ alkynyl, orthopyridyl disulfide (OPSS), halogen, and a derivative thereof, m1 to m3 are each independently a natural number of 1 to 2400, and n is a natural number of 1 to 40.

For example, $R_1$ and $R_2$ may each independently include 2,5-dioxopyrrolidinyl, 2,5-dioxopyrrolyl, aldehyde, maleimide, aryl disulfide, heteroaryl disulfide, halogenated acetamide, or a $C_{7-10}$ alkynyl. Specifically, the reactive group may be maleimide, N-hydroxysuccinimide, succinimide, form- In Formula 2 above, $L_1$ to $L_3$ are each independently a linear or branched $C_{1-6}$ alkylene, Non-Pep is a non-peptidyl polymer, m1 and m2 are each independently a natural number of 1 to 2400, and n is a natural number of 1 to 40.

In particular, in the protein complex of the present invention, the physiologically active polypeptide may be linked, by covalent bonds, to the biocompatible material via two or more reactive groups disposed at both ends of the non-peptidyl polymer-coupled fatty acid derivative compound serving as a linker.

As used herein, the term "physiologically active polypeptide", as a component constituting a moiety of the complex, refers to a polypeptide having a certain physiological function in vivo as a general concept, having a polypeptidyl structure in common, and shows various biological activities. The physiologically active polypeptide may include those capable of correcting abnormality caused by a lack or an excessive secretion of a material involved in regulation of a certain function in a living body by regulating genetic expression or physiological function and also include typical protein drugs. In addition, the physiologically active polypeptide is a concept including not only natural polypeptides but also derivatives thereof.

In the complex of the present invention, the type and size of the physiologically active polypeptide are not particularly limited as long as the physiologically active polypeptide can increase serum half-life via the structure of the complex of the present invention.

The physiologically active polypeptide of the present invention may be a hormone, a cytokine, an interleukin, an interleukin-binding protein, an enzyme, an antibody, a growth factor, a transcription factor, a blood factor, a vaccine, a structural protein, a ligand protein, a receptor, a cell surface antigen, or a receptor antagonist.

According to another embodiment, the physiologically active polypeptide included in the protein complex according to the present invention may be selected from the group consisting of: incretins regulating body weights and blood glucose levels in the stomach and intestines such as glucagon-like peptide-1 (GLP-1), glucagon-like peptide-2 (GLP-2), glucagon, gastric inhibitory polypeptide (GIP), oxyntomodulin, xenin, insulin, cholecystokinin (CCK), amylin, gastrin, ghrelin, and peptide YY (PYY); adipokines secreted from adipose such as leptin, adiponectin, adipolin, apelin, and cartonectin; neuropeptides secreted from brains such as kisspeptin, and nesfatin-1; peptides or proteins secreted from muscles such as irisin, myonectin, decorin, follistatin, and musclin; vasoactive intestinal peptide, natriuretic peptide, granulocyte colony stimulating factor (G-CSF), human growth hormone (hGH), erythropoietin (EPO), growth hormone releasing hormone, growth hormone releasing peptide, interferons, interferon receptors, G-protein-coupled receptors, interleukins, interleukin receptors, enzymes, interleukin-binding protein, cytokine-binding protein, macrophage activating factor, macrophage peptide, B cell factor, T cell factor, protein A, allergy inhibitor, cell necrosis glycoprotein, immunotoxin, lymphotoxin, tumor necrosis factor, tumor suppressor, metastasis growth factor, α-1 antitrypsin, albumin, α-lactalbumin, apolipoprotein-E, highly glycosylated erythropoietin, angiopoietins, hemoglobin, thrombin, thrombin receptor activating peptide, thrombomodulin, blood factors VII, VIIa, VIII, IX and XIII, plasminogen activating factor, fibrin-binding peptide, urokinase, streptokinase, hirudin, protein C, C-reactive protein, lenin inhibitor, collagenase inhibitor, superoxide dismutase, platelet-derived growth factor, epithelial growth factor, epidermal growth factor, angiostatin, angiotensin, bone growth factor, bone stimulating protein, calcitonin, atriopeptin, cartilage inducing factor, elcatonin, connective tissue activating factor, tissue factor pathway inhibitor, follicle stimulating hormone, luteinizing hormone, luteinizing hormone releasing hormone, nerve growth factor, parathyroid hormone, relaxin, secretin, somatomedin, insulin-like growth factor, adrenocortical hormone, cholecystokinin, pancreatic polypeptide, gastrin releasing peptide, corticotropin releasing factor, thyroid stimulating hormone, autotaxin, lactoferrin, myostatin, cell surface antigens, virus derived vaccine antigens, monoclonal antibodies, polyclonal antibodies, and antibody fragments.

According to another embodiment, the physiologically active polypeptide according to the present invention is not a naturally occurring polypeptide but selected from derivatives of naturally occurring physiologically active polypeptides. The derivatives of physiologically active polypeptides refer to polypeptides whose binding affinity to a receptor or physicochemical property is altered, i.e., water solubility is increased or immunogenicity is modified, via chemical modification such as substitution, insertion, and deletion of an amino acid, glycosylation, deglycosylation, unnatural amino acid insertion, ring insertion, and methyl residue insertion, and may also include synthetic peptides modified to have binding affinities to two or more different receptors.

As used herein, the term "physiologically active polypeptide", "physiologically active protein", "active protein", or "protein drug" refers to a polypeptide or protein having opposing physiological actions in a living body and these terms may be used interchangeably.

As used herein, the term "biocompatible material", as a component constituting a moiety of the complex, refers to a substance capable of increasing in vivo half-life when linked to the physiologically active polypeptide. As used herein, the term "biocompatible material" refers to a substance capable of increasing in vivo half-life and may be used interchangeably with "carrier". The biocompatible material or carrier may include any material capable of increasing half-life of the physiologically active polypeptide when linked thereto, and examples of the biocompatible material or carrier may include any material selected from the group consisting of polyethylene glycol (PEG), cholesterol, albumin and a fragment thereof, an albumin-binding material, a polymer of a particular amino acid sequence as a repeating unit, an antibody, an antibody fragment, an FcRn-binding material, in vivo connective tissue or a derivative thereof, a nucleotide, fibronectin, transferrin, saccharide, a polymer, and any combination thereof, without being limited thereto. The FcRn-binding material may be a polypeptide including an immunoglobulin Fc region, and examples thereof may include IgG Fc. The biocompatible material or carrier may be linked to the physiologically active polypeptide via a fatty acid derivative.

When polyethylene glycol is used as a carrier, Ambrx's ReCODE™ technology may be used for site-specific coupling of polyethylene glycol and Neose's GlycoPEGylation™ technology may be used for specific coupling to a glycan site. In addition, releasable PEG technology allowing a slow in vivo removal of polyethylene glycol may also be used, but technologies used therefor are not limited thereto, and any technologies capable of increasing in vivo availability of PEG may also be used. In addition, a polymer such as polyethylene glycol, polypropylene glycol, an ethylene glycol-propylene glycol copolymer, a polyoxyethylated polyol, a polyvinyl alcohol, a polysaccharide, a dextran, a polyvinyl ethyl ether, a biodegradable polymer, a lipid polymer, chitin, or hyaluronic acid may also be linked to the complex according to the present invention.

When albumin is used as a carrier in the present invention, the protein complex of the present invention may be a complex in which albumin or an albumin fragment is directly linked to the non-peptidyl polymer-coupled fatty acid derivative compound by covalent bonds. Although albumin is not directly linked to the non-peptidyl polymer-coupled fatty acid derivative compound, an albumin-binding material, e.g., an albumin-specific binding antibody or antibody fragment, may be linked to the non-peptidyl polymer-coupled fatty acid derivative compound in the protein complex. In addition, a protein complex in which a certain peptide, protein, compound, or the like having a binding affinity to albumin is linked to the non-peptidyl polymer-coupled fatty acid derivative compound, or a protein complex including a fatty acid having a binding affinity to albumin may also be used, but the protein complex is not limited thereto.

In the present invention, an antibody or antibody fragment may be used as a carrier, the carrier may be an antibody or antibody fragment having an FcRn-binding site or an antibody fragment not having the FcRn-binding site, such as Fab, without being limited thereto. Specifically, in the present invention, an immunoglobulin Fc region may be used as a carrier.

Since the immunoglobulin Fc region is a biodegradable polypeptide metabolized in living organisms, it is safe for use as a drug carrier. Also, since the immunoglobulin Fc region has a lower molecular weight than the entire immunoglobulin molecule, it is beneficial for preparation, purification, and yield of the complex. In addition, since the Fab region, which shows high non-homogeneity due to the difference in amino acid sequence between antibodies, is removed, the Fc region has a considerably increased homogeneity and a low potential to induce serum antigenicity.

In the present invention, the "immunoglobulin Fc region" refers to a heavy chain constant domain excluding variable domains of the heavy chain and the light chain of an immunoglobulin, a first heavy chain constant domain (CH1), and a first light chain constant domain (CL1). The Fc fragment may also include a hinge region in the heavy chain constant domain.

In addition, the immunoglobulin Fc region of the present invention may be an extended Fc fragment including the first heavy chain constant domain (CH1) and/or the first light chain constant domain (CL1) in whole or in part only excluding the variable domains of the heavy chain and the light chain of the immunoglobulin.

Because the immunoglobulin Fc region is a biodegradable polypeptide metabolized in living organisms, it is safe to use the same as a drug carrier. In addition, the immunoglobulin Fc region has a lower molecular weight compared to the entire immunoglobulin molecule, it is beneficial for preparation, purification, and yield of the complex. In addition, since the Fab region, which shows high non-homogeneity due to the difference in amino acid sequence between antibodies, is removed, the Fc region has a considerably increased homogeneity and a low potential to induce serum antigenicity.

In the present invention, the immunoglobulin Fc region includes not only a naturally occurring amino acid sequence but also a sequence mutant thereof. The amino acid sequence mutant refers to a sequence different from the naturally occurring amino acid sequence due to a deletion, insertion, non-conservative or conservative substitution, or any combination of one or more amino acids of the naturally occurring amino acid sequence. For example, in the case of IgG Fc, amino acid residues at positions 214 to 238, 297 to 299, 318 to 322, or 327 to 331, known to be important in binding, may be used as a suitable target for modification.

In addition, various types of mutants obtained by deleting a region capable of forming a disulfide bond, several amino acids from the N-terminus of a natural Fc, or adding a methionine residue to the N-terminus of the natural Fc. Furthermore, a complement-binding site, e.g., a C1q-binding site, may be removed or an antibody dependent cell mediated cytotoxicity (ADCC) region may be removed to eliminate effector functions. Techniques of preparing such sequence derivatives of the immunoglobulin Fc fragment are disclosed in International Patent Application Publication Nos. WO97/34631 and WO96/32478.

Amino acid exchanges in proteins and peptides, which do not generally alter the activity of molecules, are known in the art (H. Neurath, R. L. Hill, The Proteins, Academic Press, New York, 1979). Exchanges of amino acid residues Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and Asp/Gly are the most commonly occurring exchanges.

In some cases, the immunoglobulin Fc region may also be modified by phosphorylation, sulfation, acrylation, glycosylation, methylation, farnesylation, acetylation, amidation, etc.

The above-described Fc mutants are mutants having improved structural stability of the Fc fragment against heat, pH, or the like although they have the same biological activity as that of the Fc fragment of the present invention.

In addition, the Fc region may be obtained from naturally occurring forms isolated from humans and animals such as cows, goats, pigs, mice, rabbits, hamsters, rats and guinea pigs, or may be recombinant forms or derivatives thereof obtained from transformed animal cells or microorganisms. According to a method of obtaining from naturally occurring forms, a whole immunoglobulin is isolated from the living body of humans or animals and treated with a protease. The immunoglobulin is cleaved into Fab and Fc when treated with papain and cleaved into pF'c and F(ab)$_2$. when treated with pepsin. These fragments may be subjected, for example, to size-exclusion chromatography to isolate Fc or pF'c.

Preferably, the Fc region may be a recombinant immunoglobulin Fc region obtained from a microorganism using a human-derived Fc region.

In addition, the immunoglobulin Fc region may be in a naturally occurring glycan (sugar chain) form, an increased or decreased glycan form compared to the naturally occurring glycan form, or in a deglycosylated form. The increase, decrease, or removal of the immunoglobulin Fc glycans may be performed using conventional methods, such as a chemical method, an enzymatic method, and a genetic engineering method using a microorganism. The immunoglobulin Fc region obtained by removing glycans from the Fc region shows a sharp decrease in binding affinity for the complement (c1q) and a decrease or loss in antibody-dependent cytotoxicity or complement-dependent cytotoxicity, and thus unnecessary in vivo immune responses are not induced thereby. In this regard, an immunoglobulin Fc region in a deglycosylated or aglycosylated form may be more suitable for the purpose as a drug carrier.

As used herein, the term "deglycosylated" Fc region refers to an Fc region from which sugar moieties are removed by an enzyme, and the term "aglycosylated" Fc region refers to a non-glycosylated Fc region produced in prokaryotes, preferably, in $E.\ coli$.

Meanwhile, the immunoglobulin Fc region may originate from humans or animals such as cows, goats, pigs, mice, rabbits, hamsters, rats or guinea pigs, preferably, humans. In addition, the immunoglobulin Fc region may be an Fc fragment that is derived from IgG, IgA, IgD, IgE and IgM, any combination thereof, or any hybrid thereof. Preferably, the immunoglobulin Fc region may be derived from IgG or IgM, the most abundant protein in the human blood, and more preferably from IgG known to enhance the half-life of ligand-binding proteins.

Meanwhile, the term "combination", as used herein, refers to formation of a linkage between a polypeptide encoding a single-chain immunoglobulin Fc fragment of the same origin and a single-chain polypeptide of a different origin to form a dimer or multimer. In other words, a dimer or multimer may be formed from two or more fragments selected from the group consisting of IgG Fc, IgA Fc, IgM Fc, IgD Fc, and IgE Fc fragments.

As used herein, the term "hybrid" refers to the presence of two or more sequences corresponding to immunoglobulin Fc fragments of different origins in a single-chain immunoglobulin Fc fragment. In the present invention, various types of hybrids are possible. In other words, domain hybrids may be composed of one to four domains selected from the group consisting of CH1, CH2, CH3, and CH4 of IgG Fc, IgM Fc, IgA Fc, IgE Fc, and IgD Fc, and may include a hinge region.

Meanwhile, IgG may be divided into IgG1, IgG2, IgG3, and IgG4 subclasses, and any combination or any hybrid thereof may be used in the present invention. Preferably, IgG2 and IgG4 subclasses, and more preferably the Fc region of IgG4 rarely having effector functions such as complement-dependent cytotoxicity (CDC), may be used. In particular, the immunoglobulin Fc region for use as a drug carrier in the present invention may be a human IgG4-derived aglycosylated Fc fragment. The human Fc fragment may exhibit better effects than a non-human Fc fragment, which may act as an antigen in the human body and cause undesirable immune responses such as production of a new antibody against the antigen.

According to the present invention, a peptide or protein fragment may be used as a carrier to increase in vivo half-life. Examples of the peptide or protein fragment used herein may be an elastin like polypeptide (ELP) including a combination of certain amino acids as a repeating unit, transferrin known to have in vivo stability, fibronectin that is a component of connective tissue, or a derivative thereof, but are not limited thereto, and any peptide or protein capable of increasing in vivo half-life may be within the scope of the present invention.

As used herein, in the term "non-peptidyl polymer-coupled fatty acid derivative compound", the fatty acid, as a component constituting a moiety of the complex, generally refers to a hydrocarbon chain including one carboxyl group (—COOH), but a fatty diacid having two carboxyl groups may also be referred to as the fatty acid in the present invention. The fatty acid of the present invention may be a saturated fatty acid including only single bonds in a carbon backbone constituting the hydrocarbon chain.

In addition, in the non-peptidyl polymer-coupled fatty acid derivative compound of the present invention, the fatty acid may be a fatty acid having a normal chain structure or a fatty acid formed of an alkyl group with side chains. Fatty acids may be classified into short chain, medium chain, and long chain fatty acids according to the number of carbon atoms constituting the hydrocarbon chain. In general, short chain fatty acids include 1 to 6 carbon atoms, medium chain fatty acid include 6 to 12 carbon atoms, and long chain fatty acids include 14 or more carbon atoms.

Furthermore, the "non-peptidyl polymer-coupled fatty acid derivative compound" of the present invention may be a substance in which two or more reactive groups are respectively coupled to a fatty acid backbone directly or via a linker. For example, the reactive group may be coupled to the fatty acid backbone via a linker including a $C_{1-3}$ alkylamino chain or a $(C_{1-3}$ alkoxy$)_n(C_{1-3}$ alkylamino) chain (where n a natural number of 1 to 3), but the type of linker is not limited thereto.

The fatty acid of the non-peptidyl polymer-coupled fatty acid derivative compound of the present invention may be a carboxylic acid having a chemical formula of R—COOH or R—(COOH)$_2$, where R is a linear or branched saturated hydrocarbon group, specifically having 1 to 40 carbon atoms, more specifically 4 to 30 carbon atoms, even more specifically 10 to 25 carbon atoms, but is not limited thereto. For example, the fatty acid according to the present invention may be a fatty diacid selected from the group consisting of malonic acid ($CH_2(COOH)_2$), succinic acid ($C_2H_4(COOH)_2$), glutaric acid ($C_3H_6(COOH)_2$), adipic acid ($C_4H_8(COOH)_2$), pimelic acid ($C_5H_{10}(COOH)_2$), suberic acid ($C_6H_{12}(COOH)_2$), azelaic acid ($C_7H_{14}(COOH)_2$), sebacic acid ($C_8H_{16}(COOH)_2$), undecanedioic acid ($C_9H_{18}(COOH)_2$), dodecanedioic acid ($C_{10}H_{20}(COOH)_2$), brassylic acid ($C_{11}H_{22}(COOH)_2$), tetradecanedioic acid ($C_{12}H_{24}(COOH)_2$), pentadecanedioic acid ($C_{13}H_{26}(COOH)_2$), hexadecanedioic acid ($C_{14}H_{28}(COOH)_2$), heptadecanedioic acid ($C_{15}H_{30}(COOH)_2$), octadecanedioic acid ($C_{16}H_{32}(COOH)_2$), nonadecanedioic acid ($C_{17}H_{34}(COOH)_2$), eicosanedioic acid ($C_{18}H_{36}(COOH)_2$), henicosanedioic acid ($C_{19}H_{38}(COOH)_2$), and docosanedioic acid ($C_{20}H_{40}(COOH)_2$), more specifically, tetradecanedioic acid, pentadecanedioic acid, hexadecanedioic acid, heptadecanedioic acid, octadecanedioic acid, nonadecanedioic acid, eicosanedioic acid, henicosanedioic acid, or docosanedioic acid, but is not limited thereto.

In addition, the fatty acid of the non-peptidyl polymer-coupled fatty acid derivative compound according to the present invention may be a derivative or analogue of the above-described fatty acid. Particularly, a hydrocarbon constituting a fatty acid may be a mutant including a cyclic group in addition to the linear or branched group. The cyclic group which may be included in the hydrocarbon may be a saturated homocycle, heterocycle, aromatic condensed or non-condensed homocycle or heterocycle, and may have an ether bond, an unsaturated bond, or a substituent.

In addition, the fatty acid derivatives disclosed in U.S. Pat. No. 8,129,343 and International Patent Application Publication Nos. WO2015/067715, WO2015/055801, WO2013/041678, WO2014/133324, WO2014/009316, and WO2015/052088 may be used as the fatty acid of the non-peptidyl polymer-coupled fatty acid derivative compound according to the present invention, without limitation. For example, the fatty acid of the present invention may include, but is not limited to, a multi-fatty acid including two or more carboxyl groups, materials including a carboxylic acid (bio)isostere, a phosphoric acid, or a sulfonic acid instead of a carboxyl group of a fatty acid, fatty acid ester, and the like.

In addition, with regard to the fatty acid of the non-peptidyl polymer-coupled fatty acid derivative compound of the present invention, derivatives and analogues of the above fatty acids known in the art, and derivatives and analogues which may readily be produced in the state of the art are also within the scope of the present invention. The molecular weight of the fatty acid of the non-peptidyl polymer-coupled fatty acid derivative compound of the present invention may be in the range of 0.1 kDa to 100 kDa, specifically 0.1 kDa to 30 kDa. As the fatty acid of the non-peptidyl polymer-coupled fatty acid derivative compound of the present invention, not only a single type of a polymer but also a combination of different types of polymers may be used, without limitation.

The two or more reactive groups of the non-peptidyl polymer-coupled fatty acid derivative compound included in the protein complex of the present invention may be the same or different. For example, the fatty acid may have a maleimide group as one reactive group and an aldehyde group, such as an alkylaldehyde group, e.g., a propionaldehyde group or a butyl aldehyde, as the other reactive group.

When a fatty acid or non-peptidyl polymer including a hydroxyl reactive group as the two or more reactive groups is used, the complex of the present invention may be prepared by activating the hydroxyl group into various reactive groups via known chemical reactions or the complex may be prepared by using a commercially available fatty acid having a modified reactive group.

In the non-peptidyl polymer-coupled fatty acid derivative compound included in the protein complex of the present invention, the "non-peptidyl polymer" may be used as a generic name for biocompatible polymers including two or more repeating units binding to each other, except for peptides. The repeating units are linked together not by peptide bonds but by covalent bonds. In the present invention, the non-peptidyl polymer may be used interchangeably with a non-peptidyl linker.

The non-peptidyl polymer available in the present invention may be selected from the group consisting of a polyethylene glycol homopolymer, a polypropylene glycol homopolymer, an ethylene glycol-propylene glycol copolymer, a polyoxyethylated polyol, a polyvinyl alcohol, a polysaccharide, a dextran, a polyvinyl ethyl ether, a biodegradable polymer, a lipid polymer, a fatty acid, chitin, hyaluronic acid, and any combination thereof. Specifically, the non-peptidyl polymer may be a polyethylene glycol homopolymer, more specifically, a polymer including 1 to 2400 repeating units, but is not limited thereto. In addition, derivatives thereof well known in the art and derivatives easily manufactured by those skilled in the art may also be within the scope of the present invention.

Peptidyl linkers conventionally used in fusion proteins prepared according to a conventional inframe fusion method have drawbacks in that the peptidyl linkers are easily cleaved by proteases in living organisms, and thus, sufficient effects on increasing serum half-life of an active drug by the carrier cannot be obtained as expected. However, according to the present invention, the serum half-life of a peptide may be maintained in a similar level as that of the carrier by using a polymer having resistance to a protease. Accordingly, the non-peptidyl polymer available in the present invention is not limited as long as it has in vivo resistance to protease. A molecular weight of the non-peptidyl polymer may be greater than 0 kDa and equal to or less than 100 kDa, in the range of 1 kDa to 100 kDa, specifically greater than 0 kDa, for example, equal to or greater than 1 kDa and equal to or less than 20 kDa, or in the range of 0.5 kDa to 20 kDa, 0.5 kDa to 5 kDa, or 5 kDa to 20 kDa, but is not limited thereto. Further, the non-peptidyl polymer according to the present invention may be not only a polymer of one type but also a combination of different types of polymers.

In addition, the non-peptidyl polymer may have two or more termini, and examples thereof may include, but are not limited to, a non-peptidyl polymer having two termini and a non-peptidyl polymer having three termini.

One non-peptidyl polymer-coupled fatty acid derivative compound may include one or more types of non-peptidyl polymers.

The protein complex of the present invention may be one in which a fatty acid or non-peptidyl polymer portion of the non-peptidyl polymer-coupled fatty acid derivative compound is linked to an amino acid residue located at the N-terminus or C-terminus or in the middle, not the N-terminus or C-terminus, of the physiologically active polypeptide, and a biocompatible material is linked to the other of the fatty acid or the non-peptidyl polymer of the non-peptidyl polymer-coupled fatty acid derivative compound which is linked to the physiologically active polypeptide.

As used herein, the term "N-terminus region" refers to an amino terminus region of a peptide or protein. For example, the "N-terminus region" may include not only an amino acid residue located at the end of the N-terminus but also amino acid residues near the amino acid of the N-terminus, specifically, amino acid residues up to the $20^{th}$ amino acid residue from the end, but is not limited thereto. However, the present invention is not limited thereto.

As used herein, the term "C-terminus region" refers to a carboxyl terminus of the peptide or protein. For example, the "C-terminus region" may include not only an amino acid residue located at the end of the C-terminus but also amino acid residues near the amino acid of the C-terminus, specifically, amino acid residues up to the $20^{th}$ amino acid residue from the end, but is not limited thereto.

The protein complex of the present invention may include at least one structure of [physiologically active polypeptide-fatty acid derivative-non-peptidyl polymer-biocompatible material] and [physiologically active polypeptide-non-peptidyl polymer-fatty acid derivative-biocompatible material]. The components constituting the structure may be linked to one another in a linear or branched form by covalent bonds and the protein complex of the present invention may include at least one of each component. Because the non-peptidyl polymer-coupled fatty acid derivative compound according to the present invention may include two or more reactive groups, it may be linked to both the physiologically active polypeptide and the biocompatible material by covalent bonds, respectively. In addition, at least one conjugate, in which the physiologically active polypeptide is linked to the non-peptidyl polymer-coupled fatty acid derivative compound, is linked to the biocompatible material by covalent bonds, and accordingly, a monomer, dimer, or multimer of the physiologically active polypeptide may be formed using the biocompatible material as a mediator. Therefore, the increase in in vivo activity and stability of the physiologically active polypeptide may be achieved more effectively.

In the protein complex of the present invention, the physiologically active polypeptide may be linked to the biocompatible material in various molar ratios.

Another aspect of the present invention provides a method of preparing a protein complex including (a) linking a physiologically active polypeptide to a biocompatible material via a non-peptidyl polymer-coupled fatty acid derivative compound; and (b) separating a protein complex as a reaction product obtained in step (a).

The physiologically active polypeptide, the biocompatible material, and the non-peptidyl polymer-coupled fatty acid derivative compound are as defined above.

In step (a), the three components may be linked by covalent bonds, and the covalent bonds may occur sequentially or simultaneously. For example, when both of the physiologically active polypeptide and the biocompatible material are linked to the reactive groups of the non-peptidyl polymer-coupled fatty acid derivative compound having two or more reactive groups, it is advantageous to proceed with reactions sequentially by first linking any one of the physiologically active polypeptide and the biocompatible material to one of the reactive groups of the non-peptidyl polymer-coupled fatty acid derivative compound, and then linking the other of the physiologically active polypeptide and the biocompatible material to the other reactive group of the non-peptidyl polymer-coupled fatty acid derivative compound, to minimize production of byproducts other than the target protein complex.

Thus, step (a) may include:

(a1) linking one of the biocompatible material and the physiologically active polypeptide to one reactive group of the non-peptidyl polymer-coupled fatty acid derivative compound;

(a2) separating a conjugate in which the biocompatible material or the physiologically active polypeptide is linked to the non-peptidyl polymer-coupled fatty acid derivative compound from a reaction mixture of step (a1); and (a3) linking the other of the biocompatible material and the physiologically active polypeptide to the other reactive group of the non-peptidyl polymer-coupled fatty acid derivative compound of the conjugate separated in step (a2) to prepare a protein complex in which the two or more reactive groups of the non-peptidyl polymer-coupled fatty acid derivative compound are linked respectively to the physiologically active polypeptide and the biocompatible material, without being limited thereto.

Steps (a1) and (a3) may be performed in the presence of a reducing agent in consideration of types of the reactive groups of the non-peptidyl polymer-coupled fatty acid derivative compound participating in the reactions. Specifically, the reducing agent may be sodium cyanoborohydride (NaCNBH$_3$), sodium borohydride, dimethylamine borate, picoline borane complex, or borane pyridine.

In the method described above, steps (a2) and (b) may be performed by a method appropriately selected according to necessity among conventional methods used for separation of protein in consideration of characteristics of a product, such as required purity and molecular weight and charge of the product. For example, various known methods, including size exclusion chromatography and ion exchange chromatography, may be applied, and a plurality of different methods may be used in combination to obtain a higher purity, if required.

In step (a1), a reaction molar ratio of the physiologically active polypeptide to the non-peptidyl polymer-coupled fatty acid derivative compound and a reaction molar ratio of the biocompatible material to the non-peptidyl polymer-coupled fatty acid derivative compound may each independently be from 1:1 to 1:20. Specifically, a reaction molar ratio of the physiologically active polypeptide to the non-peptidyl polymer-coupled fatty acid derivative compound may be from 1:2 to 1:10, and a reaction molar ratio of the biocompatible material to the non-peptidyl polymer-coupled fatty acid derivative compound may be from 1:4 to 1:20. Meanwhile, in step (a3), a reaction molar ratio of the conjugate separated in step (a2) to the biocompatible material or the physiologically active polypeptide may be from 1:0.5 to 1:20, but is not limited thereto.

Another aspect of the present invention provides a protein complex prepared by the method and a pharmaceutical composition including the prepared protein complex. The pharmaceutical composition of the present invention may be a long-acting preparation having increased duration and stability in vivo when compared to a naturally occurring physiologically active polypeptide.

The pharmaceutical composition including the complex of the present invention may include a pharmaceutically acceptable carrier. For oral administration, the pharmaceutically acceptable carrier may contain a binder, a lubricant, a disintegrator, an excipient, a solubilizer, a dispersant, a stabilizer, a suspending agent, a coloring agent, a flavoring agent, and the like. For injectable preparations, the pharmaceutically acceptable carrier may contain a buffer, a preservative, an analgesic, a solubilizer, an isotonic agent, a stabilizer, and the like. For preparations for topical administration, the pharmaceutically acceptable carrier may contain a base, an excipient, a lubricant, a preservative, and the like. The pharmaceutical composition of the present invention may be formulated into various dosage forms in combination with the above-mentioned pharmaceutically acceptable carriers. For example, for oral administration, the pharmaceutical composition may be formulated into tablets, troches, capsules, elixirs, suspensions, syrups, wafers, and the like. For injectable preparations, the pharmaceutical composition may be formulated into a single-dose ampoule or multidose form. The pharmaceutical composition may also be formulated into solutions, suspensions, tablets, pills, capsules, sustained-release preparations, and the like.

Meanwhile, examples of carriers, excipients, and diluents suitable for formulation may include lactose, dextrose, sucrose, sorbitol, mannitol, xylitol, erythritol, maltitol, starch, acacia, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, and the like.

In addition, the pharmaceutical composition of the present invention may further include a filler, an anti-coagulant, a lubricant, a humectant, a flavoring agent, and a preservative, and the like.

Mode of Disclosure

Hereinafter, the present invention will be described in more detail with reference to the following examples. However, these examples are for illustrative purposes only and are not intended to limit the scope of the present invention.

Preparation Example 1: Synthesis of 2-(2-(2-aminoethoxy)ethoxy-N-(2-(2-(2,2-dimethoxyethoxy)ethoxy)ethyl)acetamide (Intermediate 1)

Reaction Scheme 1

Step 1. Preparation of Benzyl 2-(2-hydroxyethoxy)ethylcarbamate

After 2-(2-aminoethoxy)ethanol (150 mL, 1.459 mol) was dissolved in tetrahydrofuran (THF, 5 L), triethylamine (229 mL, 1.645 mol) and benzyl chloroformate (211 mL, 1.495 mol) were added thereto and the mixture was stirred for 12 hours. A solid was filtered off, washed with ethyl acetate, and a filtrate was concentrated. The concentrate was purified by column chromatography to obtain a compound (202 g) of the title.
$^1$H NMR (300 MHz, CDCl$_3$) δ 7.37-7.29 (m, 5H), 5.25 (br, 1H), 5.10 (s, 2H), 4.13-4.11 (m, 2H), 3.57-3.54 (m, 4H), 3.43-3.38 (m, 2H), 2.24 (br, 1H).

Step 2. Preparation of t-butyl 3-oxo-1-phenyl-2,7,10-trioxa-4-azadodecan-12-oate After the benzyl 2-(2-hydroxyethoxy)ethylcarbamate (129 g, 0.539 mol) obtained in Step 1 was dissolved in THF (2 L), potassium t-butoxide (60.5 g, 0.593 mol) was added dropwise thereto at 0° C. After 30 minutes, t-butyl bromo acetate was added thereto and stirred at 0° C. for 3 hours and further stirred at room temperature for 15 hours. The reaction was terminated by adding water to the reaction solution, the resultant was concentrated and extracted with ethyl acetate. An organic layer was dried over anhydrous magnesium sulfate and filtered. A filtrate was concentrated and purified by column chromatography to obtain a compound (87.5 g) of the title.
$^1$H NMR (300 MHz, CDCl$_3$) δ 7.36-7.30 (m, 5H), 5.38 (br, 1H), 5.10 (s, 2H), 4.00 (s, 2H), 3.70-3.64 (m, 4H), 3.60-3.56 (m, 2H), 3.43-3.40 (m, 2H), 1.46 (s, 9H).

Step 3. Preparation of 3-oxo-1-phenyl-2,7,10-trioxa-4-azadodecan-12-oic Acid After the t-butyl 3-oxo-1-phenyl-2,7,10-trioxa-4-azadodecan-12-oate (9.5 g, 26.880 mmol) obtained in Step 2 was dissolved in dichloromethane (32 mL), trifluoroacetic acid (32 mL) was added thereto and the mixture was stirred at room temperature for 5 hours. The reaction solution was filtered and a filtrate was concentrated to obtain a compound (7.1 g) of the title.
$^1$H NMR (300 MHz, CDCl$_3$) δ 7.36-7.31 (m, 5H), 5.24 (s, 1H), 5.11 (s, 2H), 4.15 (s, 2H), 3.75-3.59 (m, 6H), 3.43-3.41 (m, 2H).

Step 4. Preparation of ethyl 3-oxo-1-phenyl-2,7,10-trioxa-4-azadodecan-12-oate After the benzyl 2-(2-hydroxyethoxy)ethylcarbamate (20.0 g, 83.588 mmol) obtained in Step 1 was dissolved in THF (320 mL), potassium t-butoxide (9.4 g, 83.588 mmol) was added dropwise thereto at 0° C. After 30 minutes, ethyl bromo acetate (11.5 mL, 100.305 mmol) was added thereto, and the mixture was stirred at 0° C. for 3 hours and further stirred at room temperature for 15 hours. Upon completion of the reaction by adding water to the reaction solution, the resultant was concentrated and extracted with ethyl acetate. An organic layer was dried over anhydrous magnesium sulfate and filtered, and a filtrate was concentrated and purified to obtain a compound (9.5 g) of the title.
$^1$H NMR (300 MHz, CDCl$_3$) δ 7.36-7.30 (m, 5H), 5.32 (br, 1H), 5.10 (s, 2H), 4.19 (q, 2H), 4.12 (s, 2H), 3.72-3.65 (m, 4H), 3.59-3.56 (m, 2H), 3.41-3.38 (m, 2H), 1.26 (t, 3H).

Step 5. Preparation of 2-(2-(2,2-dimethoxyethoxy)ethoxy)ethane-1-amine

After the ethyl 3-oxo-1-phenyl-2,7,10-trioxa-4-azadodecan-12-oate (9.5 g, 29.198 mmol) obtained in Step 4 was dissolved in anhydrous THF (60 mL), diisobutylaluminum hydride (DIBAL-H, 43.8 mL, 23.051 mmol) was slowly added dropwise thereto in an argon atmosphere at −78° C. and the mixture was stirred at 0° C. for 1 hour. 10% hydrochloric acid was slowly added to the reaction solution, and the mixture was stirred at 0° C. for 30 minutes, followed by extraction with ethyl acetate. An organic layer was dried over anhydrous magnesium sulfate and filtered, and a filtrate was concentrated. After a product was dissolved in methanol (36 mL) in an argon atmosphere, trimethyl orthoformate (25.6 mL, 233.587 mmol) and p-toluene sulfonic acid (278 mg, 1.460 mmol) were added thereto, and the mixture was stirred at room temperature for 2 hours. The mixture was subjected for extraction with ethyl acetate, and an organic layer was dried over anhydrous magnesium sulfate and filtered, and a filtrate was concentrated and purified by column chromatography. After a product was dissolved in methanol (40 mL), 10% Pd/C (780 mg, 0.4 wt %) was added thereto, and the mixture was stirred in a hydrogen atmosphere at room temperature for 3 hours. The reaction solution was filtered, and a filtrate was dried to obtain a compound (1.2 g) of the title.
$^1$H NMR (300 MHz, CDCl$_3$) δ 4.66 (br, 2H), 4.54 (t, 1H), 3.74-3.64 (m, 6H), 3.65 (d, 2H), 3.41 (s, 6H), 3.01 (t, 2H).

Step 6. Preparation of 2-(2-(2-aminoethoxy)ethoxy)-N-(2-(2-2,2-dimethoxyethoxy)ethoxy)ethyl)acetamide

After the 3-oxo-1-phenyl-2,7,10-trioxa-4-azadodecan-12-oic acid (1.2 g, 5.951 mmol) obtained in Step 3 was dissolved in acetonitrile (70 mL), (benzotriazol-1-yloxy)tris(dimethylamino)phosphonium hexafluorophosphate (BOP, 2.8 g, 6.235 mmol) and N,N-diisopropylethylamine (DIPEA, 3.0 mL, 17.003 mmol) were added thereto, and the mixture was stirred at room temperature for 30 minutes. The 2-(2-(2,2-dimethoxyethoxy)ethoxy)ethane-1-amine (1.7 g, 5.668 mmol) obtained in Step 5 was added to the reaction solution, and the mixture was stirred at room temperature for 3 hours. Upon completion of the reaction, ethyl acetate was added thereto, and the mixture was washed with sodium bicarbonate. Then, the resultant was dried over anhydrous magnesium sulfate and filtered, and a filtrate was concentrated and purified by column chromatography. A product was dissolved in methanol (30 mL), 10% Pd/C (640 mg, 0.4 wt %) was added thereto, and the mixture was stirred in a hydrogen atmosphere at room temperature for 3 hours. The reaction solution was filtered, and a filtrate was concentrated and dried to obtain a compound (Intermediate 1, 1.0 g) of the title.

$^1$H NMR (300 MHz, CDCl$_3$) δ 4.51 (t, 1H), 4.02 (s, 2H), 3.71-3.49 (m, 16H), 3.41 (s, 6H), 2.94 (t, 2H).

Preparation Example 2: Synthesis of 2,5-dioxopyrrolidine-1-yl (S)-24-(t-butoxycarbonyl)-3-methoxy-12,21,26-trioxo-2,5,8,14,17-pentaoxa-11,20,25-triazatritetracontan-43-oate (Intermediate 2)

Reaction Scheme 2

Step 1. Preparation of 18-(benzyloxy)-18-oxooctadecanoic Acid

Octadecandioic acid (100 g, 318 mmol), p-toluene sulfonic acid (756 mg, 3.975 mmol), and benzyl alcohol (26.4 mL, 254.4 mol) were added to toluene (3.7 L, and the mixture was distilled. Celite was added to the reaction solution, and the mixture was cooled to 40° C., stirred for 1 hour, and filtered through silica gel. A filtrate was concentrated under reduced pressure and heptane was added thereto at 50° C. A solid was filtered and washed with heptane, and dried to obtain a compound (67.9 g) of the title.

$^1$H NMR (300 MHz, CDCl$_3$) δ 7.36-7.34 (m, 5H), 5.11 (s, 2H), 2.35 (t, 4H), 1.64 (t, 4H), 1.25 (s, 24H).

Step 2. Preparation of 1-benzyl 18-(2,5-dioxopyrrolidine-1-yl) octadecandioate After dissolving the 18-(benzyloxy)-18-oxooctadecanoic acid (20.0 g, 49.433 mmol) obtained in Step 1 in N-hydroxysuccinimide (6.8 g, 59.319 mmol) and dissolving N,N'-diisopropylcarbodiimide (DIC, 12.24 g, 59.312 mmol) in N-methyl-2-pyrrolidone (NMP, 200 mL), the mixtures were stirred at 60° C. for 2.5 hours. Upon completion of the reaction, the reaction solution was cooled to room temperature and filtered to obtain a solid. Water was added to a filtrate and the produced solid was filtered out and washed with water. The solid was recrystallized with isopropylalcohol to obtain a compound (21.6 g) of the title.

$^1$H NMR (300 MHz, CDCl$_3$) δ 7.37-7.31 (m, 5H), 5.11 (s, 2H), 2.83 (s, 2H), 2.60 (t, 2H), 2.35 (t, 2H), 1.77-1.53 (m, 6H), 1.25 (s, 24H).

Step 3. Preparation of (S)-1-t-butyl 5-(2,5-dioxopyrrolidine-1-yl) 2-(18-(benzyloxy)-18-oxooctadecanamido)pentanedioate The 1-benzyl 18-(2,5-dioxopyrrolidine-1-yl) octadecandioate (9.0 g, 17.940 mmol) obtained in Step 2 and L-glutamic acid 5-t-butyl ester (3.8 g, 18.837 mmol) were added to NMP (80 mL), and the mixture was stirred at 50° C. for 4 hours. Upon completion of the reaction, the reaction solution was cooled to room temperature, and water (230 mL), 0.5 M potassium bisulfate (34 mL), and ethyl acetate were added thereto, and then the mixture was extracted. An organic layer was dried over anhydrous magnesium sulfate and filtered, and a filtrate was concentrated. A product was dissolved in NMP (68 mL), and N-hydroxysuccinimide (3.3 g, 28.705 mmol) and N,N'-dicyclohexylcarbodiimide (DCC, 4.8 g, 23.323 mmol) were added thereto, and then the mixture was stirred at room temperature for 16 hours. A solid was filtered and a filtrate was washed with water. An organic layer was dried over anhydrous magnesium sulfate and filtered, and the filtrate was concentrated. A concentrate was purified by column chromatography to obtain a compound (4.9 g) of the title.

$^1$H NMR (300 MHz, CDCl$_3$) δ 7.36-7.32 (m, 5H), 6.24 (d, 1H), 5.12 (s, 2H), 4.62-4.60 (m, 1H), 3.39 (t, 2H), 2.85 (s, 4H), 2.80-2.73 (m, 2H), 2.33 (t, 2H), 2.25-2.00 (m, 2H), 1.67-1.63 (m, 4H), 1.48 (s, 9H), 1.25 (s, 24H).

Step 4. Preparation of (S)-24-(t-butoxycarbonyl)-3-methoxy-12,21,26-trioxo-2,5,8,14,17-pentaoxa-11,20,25-triazatritetracontan-43-oic Acid The (S)-1-t-butyl 5-(2,5-dioxopyrrolidine-1-yl) 2-(18-(benzyloxy)-18-oxooctadecanamido)pentanedioate (1.9 g, 2.814 mmol) obtained in Step 3, Intermediate 1 (1.0 g, 2.955 mmol) prepared according to Preparation Example 1, and triethylamine (1.2 mL, 8.443 mmol) were added to acetonitrile (40 mL), and the mixture was stirred at room temperature for 16 hours. Upon completion of the reaction, the reaction solution was concentrated and purified by column chromatography. A product was dissolved in methanol (80 mL) and 10% Pd/C (600 mg, 0.4 wt %) was added thereto, and the mixture was stirred in a hydrogen atmosphere at room temperature for 3 hours. After filtering the reaction solution, a filtrate was concentrated and dried under a reduced pressure to obtain a compound (1.1 g) of the title.

$^1$H NMR (300 MHz, CDCl$_3$) δ 7.21 (br, 1H), 6.87 (br, 1H), 6.66 (d, 1H), 4.52 (t, 1H), 4.41-4.37 (m, 1H), 4.03 (s, 2H), 3.70-3.47 (m, 18H), 3.40 (s, 6H), 2.36-2.20 (m, 7H), 1.93-1.86 (m, 1H), 1.63-1.61 (m, 4H), 1.46 (s, 9H), 1.25 (s, 24H).

Step 5. Preparation of (S)-2,5-dioxopyrrolidine-1-yl 24-(t-butoxycarbonyl)-3-methoxy-12,21,26-trioxo-2,5,8,14,17-pentaoxa-11,20,25-triazatetracontan-43-oate

After the (S)-24-(t-butoxycarbonyl)-3-methoxy-12,21,26-trioxo-2,5,8,14,17-pentaoxa-11,20,25-triazatritetracontan-43-oic acid (1.1 g, 1.293 mmol) obtained in Step 4 was dissolved in dichloromethane (35 mL), N-hydroxysuccinimide (164 mg, 1.422 mmol) and 1-ethyl-3-(3-dimethylaminopropyl)carbodiimide (EDC, 297 mg, 1.551 mmol) were added thereto, and then the mixture was stirred at room temperature for 16 hours. Upon completion of the reaction, the resultant was washed with sodium bicarbonate and dried over anhydrous magnesium sulfate. The resultant was filtered, and the filtrate was concentrated and purified by column chromatography to obtain a compound (Intermediate 2, 778 mg) of the title.

$^1$H NMR (300 MHz, CDCl$_3$) δ 7.20 (br, 1H), 6.75 (br, 1H), 6.54 (d, 1H), 4.51 (t, 1H), 4.43-4.40 (m, 1H), 4.01 (s, 2H), 3.70-3.47 (m, 18H), 3.39 (s, 6H), 2.84 (s, 4H), 2.60 (t, 2H), 2.29-2.19 (m, 5H), 1.99-1.98 (m, 1H), 1.75 (t, 2H), 1.63-1.59 (m, 2H), 1.25 (s, 24H);

MS(ESI$^+$): [M+H]$^+$ m/z 917.6.

Example 1: Preparation of Non-Peptidyl Polymer-Coupled Fatty Acid Derivative Compound Having Aldehyde Groups at Both Ends (Ald-PEG-FA)

Reaction Scheme 3

Step 1. Preparation of Non-Peptidyl
Polymer-Coupled Fatty Acid Derivative Compound
with Acetal Groups Introduced at Both Ends
(Acetal-PEG-FA)

Acetal-PEG-amine (3.4 kDa, n=77 in average, 370 mg, 0.11 mmol) was dissolved in dichloromethane (22 mL), and triethylamine (23 μL, 0.164 mmol) and Intermediate (2 50 mg, 0.055 mmol) prepared according to Preparation Example 2 were added thereto, and then the mixture was stirred at room temperature for 16 hours. Upon completion of the reaction, the reaction solution was concentrated and purified by MPLC to obtain a compound (60 mg) of the title.
MS: MW 4100-4400.

Step 2. Preparation of Non-Peptidyl
Polymer-Coupled Fatty Acid Derivative Compound
with Acetal Groups Introduced at Both Ends
(Ald-PEG-FA)

The Acetal-PEG-FA (30 mg, 0.007 mmol) obtained in Step 4 was dissolved in dichloromethane (1 mL), and trifluoroacetic acid (53 μL, 0.714 mmol) was added thereto, and then the mixture was stirred at room temperature for 24 hours. Upon completion of the reaction, the reaction solution was concentrated and recrystallized with diethylether to obtain a compound (18 mg) of the title.
MS: MW 3900-4300.

Example 2: Linking Physiologically Active
Polypeptide to Non-Peptidyl Polymer-Coupled
Fatty Acid Derivative In order to link the non-peptidyl polymer-coupled fatty acid derivative compound, as a linker, with aldehyde groups, as reactive groups, introduced at both ends prepared in Example 1 to the N-terminus of an insulin beta chain that is one type of the physiologically active polypeptide, insulin powder (Biocon, India) was dissolved in 10 mM HCl. The insulin solution was mixed with the linker in a molar ratio of 1:2, and a concentration of insulin was adjusted to 5 mg/mL, followed by reaction at room temperature for 2 hours. In this case, the reaction was performed by adding a sodium cyanoborohydride (SCB; $NaCNBH_3$) reducing agent thereto in a mixed solvent of a 50 mM sodium citrate buffer solution (pH 5.0) and isopropanol. The reaction solution was purified using a buffer including sodium citrate (pH 3.0) and ethanol and an SP-HP column (GE, USA) employing a potassium concentration gradient.

Figure 1:
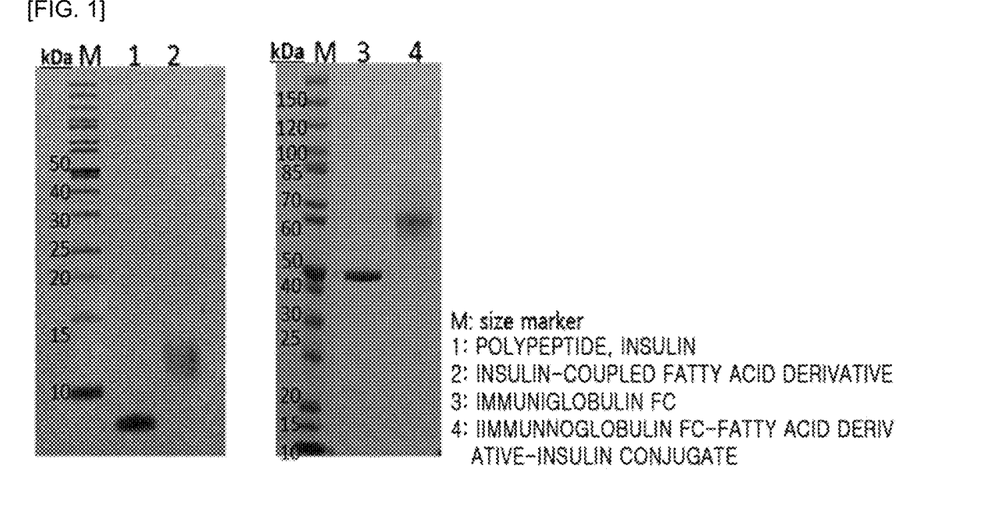
FIG. 1 shows results of SDS-PAGE analysis to identify synthesis of an immunoglobulin Fc-fatty acid derivative-insulin complex according to the present invention.
Figure 2:
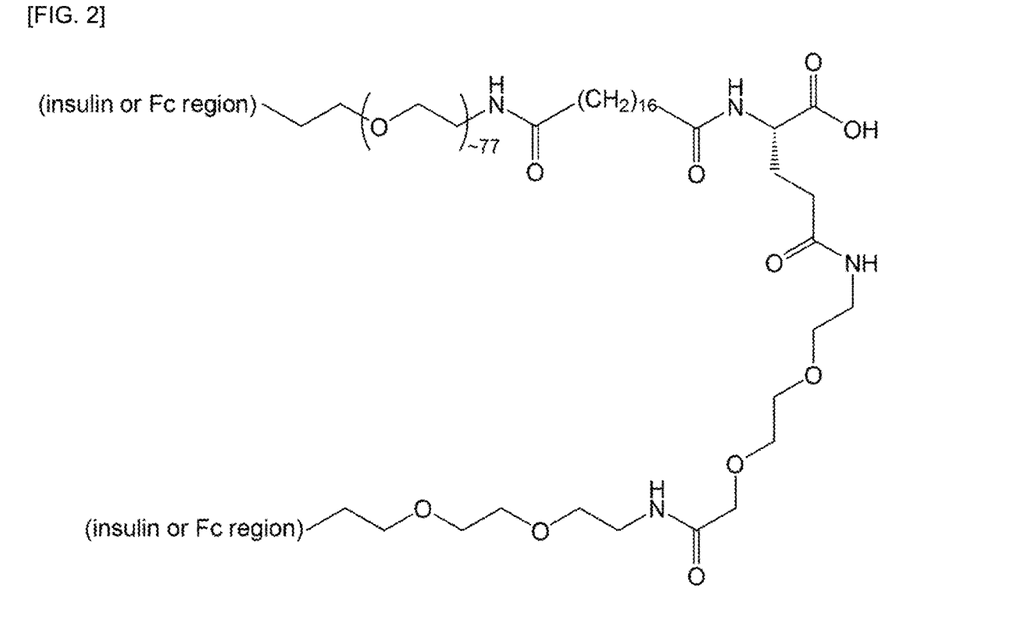
FIG. 2 is a structural formula of an immunoglobulin Fc-fatty acid derivative-insulin complex prepared according to an embodiment of the present invention.

Example 3: Preparation of Protein Complex in
which Immunoglobulin Fc is Linked to
Non-Peptidyl Polymer-Coupled Fatty Acid
Derivative Compound Then, in order to link the conjugate prepared according to Example 2, in which the non-peptidyl polymer-coupled fatty acid derivative compound is linked to insulin, to the N-terminus of an immunoglobulin Fc fragment, one type of the biocompatible material, the conjugate of Example 2 was mixed with the immunoglobulin Fc fragment in a molar ratio of 1:10, and a total concentration of proteins was adjusted to 20 mg/mL, followed by reaction at 25° C. for 12 to 18 hours. In this case, a 100 mM HEPES buffer solution (pH 8.2) including sodium chloride was used as a reaction solution, and a 20 mM sodium borohydride was added thereto as a reducing agent. Upon completion of the reaction, the reaction solution was purified with a Tris buffer solution (pH 7.5) and a Q-HP column (GE, USA) using a calcium chloride concentration gradient, and then unreacted proteins were separated using a size exclusion chromatography column (Superdex 200, GE, USA). Furthermore, only the complex in which the insulin is linked to the immunoglobulin Fc fragment via the non-peptidyl polymer-coupled fatty acid derivative compound linker by covalent bonds was purified by using a Source 15 Q column (GE, USA) which uses sodium chloride and a Tris (pH 6.0) concentration gradient. The prepared protein complex was confirmed by SDS-PAGE (FIG. 1).

Example 4: Confirmation of In Vivo
Pharmacokinetics of Protein Complex

In vivo pharmacokinetics of the protein complex prepared according to Example 3 was confirmed, and in vivo duration thereof was compared with that of existing insulin. Specifically, SD rats, which are widely used as normal animal models, were used for confirmation of pharmacokinetics. Non-fasting 8-week-old normal rats were classified into the following groups: a human insulin-administered group (172 nmol/kg), an immunoglobulin Fc-PEG-insulin complex-administered group (3.88 nmol/kg), and a group administered with the protein complex of Example 3, i.e., immunoglobulin Fc-non-peptidyl polymer-coupled fatty acid derivative-insulin complex (hereinafter, referred to as 'immunoglobulin Fc-fatty acid derivative-insulin' in the following examples and drawings for descriptive convenience) (3.88 nmol/kg). The test substances were subcutaneously injected once into three normal rats of each group. Whole blood was collected by tail vein blood collection from the human insulin-administered group at 0.25, 0.75, 1, 1.5, 2, 3 and 5, from the immunoglobulin Fc-PEG-insulin complex-administered group and the immunoglobulin Fc-fatty acid derivative-insulin complex-administered group that is the protein complex of Example 3 at 1, 4, 8, 24, 48, 72, 96, 120 and 144 hours. Sera was separated from the collected whole blood by centrifugation at 5,000 rpm for 10 minutes at room temperature in a 1.5 mL-microtube and stored at −20° C. The serum was subjected to the enzyme-linked immunosorbent assay (ELISA) to quantify a concentration of the insulin complex included in the serum of each group. The ELISA was performed by simultaneously adding the serum collected at each time and anti-human IgG4-HPR (Alpha Diagonosis, #10124) onto a plate coated with insulin monoclonal antibody (ALPCO, #80-INSHU-E10.1), performing reaction for 1 hour at room temperature and chromogenic reaction with a TMB reagent, and then measuring absorbance at a wavelength of 450 nm. Pharmacokinetic parameters were calculated using Phoenix™ WinNonin 7.0 based on blood concentration per hour and shown in FIG. 3.

Figure 3:
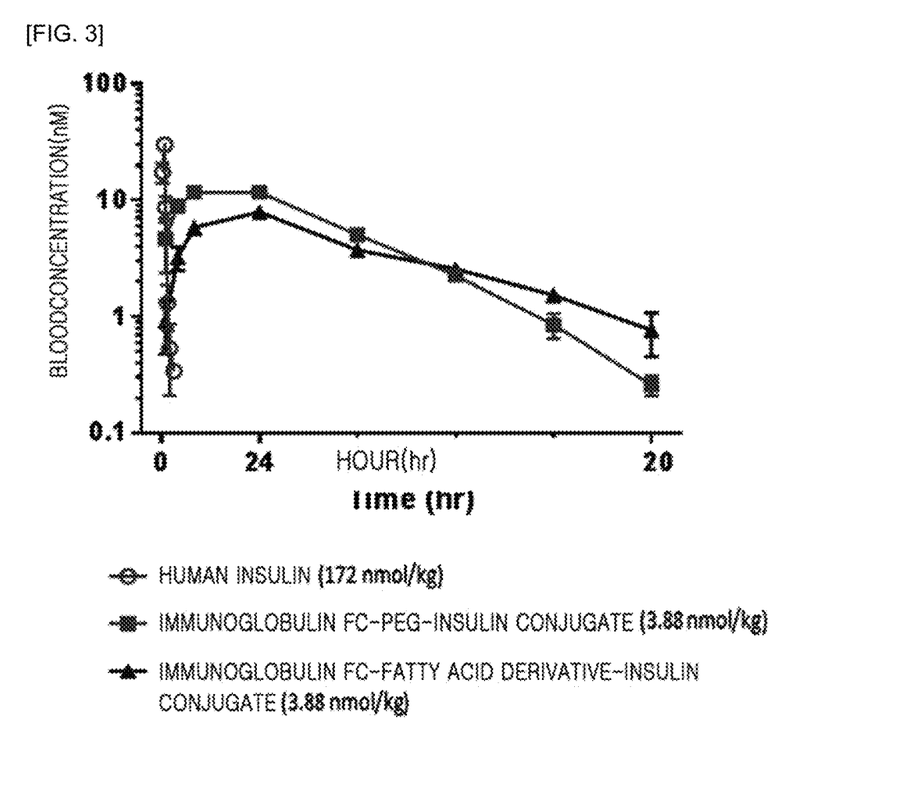
FIG. 3 is a graph illustrating pharmacokinetic analysis results of an immunoglobulin Fc-fatty acid derivative-insulin complex according to the present invention. For comparison, blood concentrations of the immunoglobulin Fc-fatty acid derivative-insulin complex-administered group with time were shown together with results of a human insulin-administered group and an immunoglobulin Fc-PEG-insulin complex-administered group.

As shown in FIG. 3, durations of all of the immunoglobulin Fc-PEG-insulin complex and the immunoglobulin Fc-fatty acid derivative-insulin complex were significantly increased when compared with human insulin. Particularly, half-lives of the immunoglobulin Fc-fatty acid derivative-insulin complex and the immunoglobulin Fc-PEG-insulin complex measured when administered at the same dose were 35.8 hours and 14.8 hours, respectively. This indicates that in vivo duration of the immunoglobulin Fc-fatty acid derivative-insulin complex according to the present invention increased. Particularly, the results also indicate excellent effects of the non-peptidyl polymer-coupled fatty acid derivative as a novel linker.

These results suggest that the non-peptidyl polymer-coupled fatty acid derivative linker according to the present invention, which links the physiologically active polypeptide to the biocompatible material significantly, may significantly increase the duration of the physiologically active polypeptide linked thereto providing a status as a new drug platform capable of reducing dose and frequency of administration.

The above description of the present invention is provided for the purpose of illustration, and it would be understood by those skilled in the art that various changes and modifications may be made without changing technical conception and essential features of the present invention. Thus, it is clear that the above-described embodiments are illustrative in all aspects and do not limit the present invention. The scope of the invention is defined by the appended claims rather than by the description preceding them, and therefore all changes and modifications that fall within metes and bounds of the claims, or equivalents of such metes and bounds are therefore intended to be embraced by the claims.

The invention claimed is:

1. A non-peptidyl polymer-coupled fatty acid derivative compound of Formula 1 below, a stereoisomer thereof, or a pharmaceutically acceptable salt thereof:

Formula 1 wherein $L_1$ to $L_3$ are each independently a linear or branched $C_{1-6}$ alkylene,

$R_1$ and $R_2$ are each independently selected from the group consisting of aldehyde, maleimide, a $C_{6-20}$ aryl disulfide, a $C_{5-20}$ heteroaryl disulfide, vinyl sulfone, thiol, a halogenated acetamide, succinimide, p-nitrophenyl carbonate, a $C_{7-10}$ alkynyl, orthopyridyl disulfide (OPSS), and a halogen, m1 to m3 are each independently a natural number of 1 to 2400, and n is a natural number of 1 to 40.

2. A non-peptidyl polymer-coupled fatty acid derivative compound of Formula 1 below, a stereoisomer thereof, or a pharmaceutically acceptable salt thereof:

Formula 1 wherein $L_1$ to $L_3$ are each independently a linear or branched $C_{1-6}$ alkylene, $R_1$ and $R_2$ are each independently maleimide, N-hydroxysuccinimide, succinimide, formaldehyde, acetaldehyde, propionaldehyde, butylaldehyde, orthopyridyl disulfide (OPSS), iodoacetamide, bromoacetamide, fluoroacetamide, chloroacetamide, astatinoacetamide, tennessinoacetamide, or a $C_{7-10}$ alkynyl m1 to m3 are each independently a natural number of 1 to 2400, and n is a natural number of 1 to 40.

3. A method of preparing a protein complex, the method comprising:

(a) linking a physiologically active polypeptide to a biocompatible material via a non-peptidyl polymer-coupled fatty acid derivative compound of the following Formula 1:

Formula 1 wherein $L_1$ to $L_3$ are each independently a linear or branched $C_{1-6}$ alkylene, $R_1$ and $R_2$ are each independently selected from the group consisting of aldehyde, maleimide, a $C_{6-20}$ aryl disulfide, a $C_{5-20}$ heteroaryl disulfide, vinyl sulfone, thiol, a halogenated acetamide, succinimide, p-nitrophenyl carbonate, a $C_{7-10}$ alkynyl, orthopyridyl disulfide (OPSS), and a halogen, m1 to m3 are each independently a natural number of 1 to 2400, and n is a natural number of 1 to 40; and (b) separating a protein complex as a reaction product obtained in the step (a).

4. The method according to claim 3, wherein the step (a) comprises:
(a1) linking one of the biocompatible material and the physiologically active polypeptide to one reactive group of the non-peptidyl polymer-coupled fatty acid derivative compound of Formula 1;
(a2) separating a conjugate in which the biocompatible material or the physiologically active polypeptide is linked to the non-peptidyl polymer-coupled fatty acid derivative compound from a reaction mixture of the step (a1); and
(a3) linking the other of the biocompatible material and the physiologically active polypeptide to one or more reactive group of the non-peptidyl polymer-coupled fatty acid derivative compound of the conjugate separated in the step (a2) to prepare a protein complex in which the two or more reactive groups of the non-peptidyl polymer-coupled fatty acid derivative compound are linked to the physiologically active polypeptide and the biocompatible material.

5. The method according to claim 4, wherein the steps (a1) and (a3) are performed in the presence of a reducing agent.

6. The method according to claim 5, wherein the reducing agent is sodium cyanoborohydride ($NaCNBH_3$), sodium borohydride, dimethylamine borate, picoline borane complex, or borane pyridine.

7. The method according to claim 4, wherein a molar ratio of the physiologically active polypeptide to the non-peptidyl polymer-coupled fatty acid derivative compound of Formula 1 is from 1:1 to 1:20 and a molar ratio of the biocompatible material to the non-peptidyl polymer-coupled fatty acid derivative compound of Formula 1 is from 1:1 to 1:20 in the step (a1).

8. The method according to claim 4, wherein a molar ratio of the conjugate separated in the step (a2) to the biocompatible material or the physiologically active polypeptide is from 1:0.5 to 1:20 in the step (a3).

* * * * *